United States Patent [19]

Smialek et al.

[11] 4,220,769

[45] Sep. 2, 1980

[54] CYANURIC ACID MANUFACTURE

[75] Inventors: Raymond J. Smialek, Lake Charles, La.; Neal E. Morganson, Pittsburgh, Pa.

[73] Assignee: Olin Corporation, New Haven, Conn.

[21] Appl. No.: 54,083

[22] Filed: Jul. 2, 1979

[51] Int. Cl.$^2$ .......................................... C07D 251/32
[52] U.S. Cl. ................................................... 544/192
[58] Field of Search ........................................ 544/192

[56] References Cited

FOREIGN PATENT DOCUMENTS 890814 3/1962 United Kingdom .

Primary Examiner—John M. Ford
Attorney, Agent, or Firm—James B. Haglind; Donald F. Clements

[57] ABSTRACT

A process for producing cyanuric acid by pyrolyzing urea in a solvent in a closed reactor having interior surfaces exposed to a gas zone, the improvement which comprises contacting the interior surfaces of the closed reactor with solvent in the presence of heat to inhibit the formation of solid deposits on the interior reactor surfaces.

The process maintains high rates of heat transfer during the reaction period and reduces the frequency and cost of reactor cleaning.

8 Claims, 1 Drawing Figure

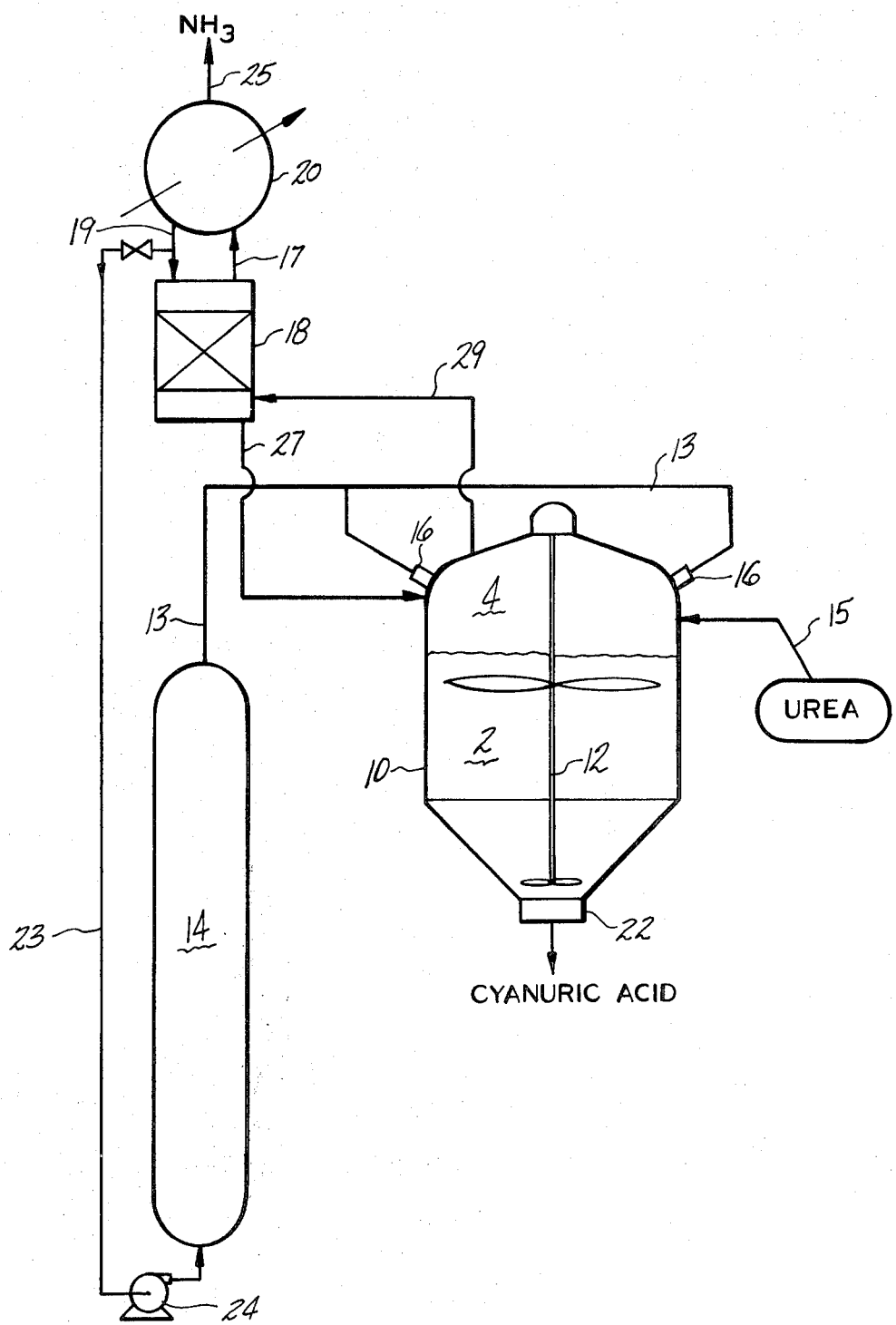

CYANURIC ACID MANUFACTURE

This invention relates to the production of cyanuric acid. More particularly, this invention relates to the production of cyanuric acid from the pyrolysis of urea in a solvent.

Cyanuric acid can be produced by heating urea or biuret in a solvent medium. During the process, solid particles of cyanuric acid are formed in the hot solvent. Copious amounts of ammonia gas are also produced. The evolving ammonia, in combination with hot solvent vapors forms a gaseous mixture which entrains cyanuric acid particles and deposits them on reactor surfaces. The amount of deposition increases in proportion to the concentration of cyanuric acid. A buildup of these deposits substantially reduces the rate of heat transfer through reactor surfaces which then requires a reduction in the urea feed rate and subsequently the production rate of cyanuric acid. Further, solid deposits also decrease the gas space in the reactor and promote the carry-over of solids into the gas and solvent recovery operations. In addition, periodic shutdowns of the process are required for extensive and thus expensive cleaning efforts to remove the deposits from the reactor surfaces.

It is an object of the present invention to provide a process for producing cyanuric acid in a solvent medium where scaling of reactor surfaces is eliminated or minimized.

Another object of the present invention is to provide a process for producing cyanuric acid whereby maximum heat transfer efficiency is attained.

A further object of the present invention is to provide a process for producing cyanuric acid where reactor maintenance costs are minimized.

These and other objects of the invention are accomplished in a process for producing cyanuric acid by pyrolyzing urea in a solvent in a closed reactor having interior surfaces exposed to a gas zone, the improvement which comprises contacting said interior surfaces in said gas zone with the solvent in the presence of heat to inhibit the formation of solid deposits on the interior surfaces.

The FIGURE presents a flow diagram of the novel process of the present invention.

Hot solvent from heater 14 is charged to reactor 10 through nozzles 16 fed by line 13. Molten urea is fed to reactor 10 through line 15. During the pyrolysis reaction, cyanuric acid particles and ammonia gas are formed in slurry zone 2. Agitator 12 stirs the reaction mixture to keep cyanuric acid particles in suspension. A hot gaseous mixture of ammonia and solvent vapors having cyanuric acid particles entrained therein accumulates in gas zone 4. The hot gaseous mixture contacts interior reactor surfaces in gas zone 4 before being passed from reactor 10 to a scrubber 18 through line 29. The scrubbed gaseous mixture passes through line 17 to condenser 20. Condensed liquid solvent returns to scrubber 18 through line 19. From scrubber 18, condensed liquid solvent passes through line 27 to reactor 10. Condensed solvent may also be directed through supply pump 24 into heater 14 via line 23. Ammonia gas is removed from condenser 18 through line 25. Following the pyrolysis reaction, a slurry of cyanuric acid is removed from reactor 10 through outlet 22 for further processing.

In the pyrolysis process, urea is fed to a reactor containing a body of solvent. The solvent is maintained at temperatures sufficient to pyrolyze the urea, for example, in the range of from about 150° to about 300° C. During the pyrolysis process, the urea is converted to cyanuric acid in a reaction which is believed to be expressed by the following equation:

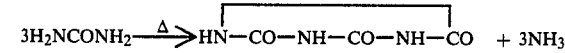

$$3H_2NCONH_2 \xrightarrow{\Delta} \overline{HN-CO-NH-CO-NH-CO} + 3NH_3$$

The solvent selected is preferably one in which the cyanuric acid has a low order of solubility. Solid particles of cyanuric acid produced are kept in suspension by agitating the reaction mixture using, for example, mechanical or gas agitation means.

Ammonia gas is also produced in large amounts and during the reaction period mixes with hot solvent vapors and minor amounts of carbon dioxide to form a gaseous mixture. As this gaseous mixture rises and separates from the reaction mixture, it entrains particles of cyanuric acid and deposits them on reactor surfaces in the gas zone above the reaction mixture. Deposits can form on any surfaces which are not regularly wetted by the solvent in the reaction mixture. Particularly heavy deposits of solvated cyanuric acid particles can accumulate on the dome of the reactor and the sides of the reactor in the gas zone when concentrated slurries are produced. These deposits reduce heat transfer rates of the reactor surfaces. They also decrease the gas space in the reactor and promote the carryover of reactor solids into the solvent and ammonia recovery systems.

In the novel process of the present invention, the reactor surfaces in the gas zone above the reaction mixture are contacted with solvent to prevent the build-up of deposits of cyanuric acid particles. To effectively inhibit deposit build-up, it is necessary that heat be present while the solvent is applied to the reactor surfaces. Heat may be supplied, for example, by employing the hot solvent used in the pyrolysis reaction or by heating the reactor surfaces, for example, through heating coils to a temperature in the range of from about 100° to about 300° C., preferably from about 150° to about 250° C.

Solvent can be flowed or sprayed over the reactor surfaces continuously during the reaction period, or applied intermittently, for example, by spraying. Other means of applying the solvent to the reactor surfaces include a distributor selected to divert condensed reflux solvent onto the reactor surfaces; or a plate or disc fastened to the agitator which centrifugally hurls solvents against the reactor surfaces. Where spraying is used, devices such as spray nozzles are employed which effectively cover the surface areas with solvent, preferably under pressures sufficient to remove any deposits present or to inhibit deposit formation. Any suitable spray pressures may be used to apply the solvent, depending on the spray devices selected. From a practical point of view, suitable spray pressures are those, for example, in the range of from about 20 to about 100, and preferably at from about 30 to about 60 pounds per square inch.

Where a batch process is used to produce cyanuric acid, deposits can be inhibited or effectively removed from reactor surfaces by applying the solvent between batches.

The quantity of solvent applied to the reactor surfaces is not critical as all of the solvent used in the pyrolysis may be employed in this manner or as little as a few percent of the total quantity of solvent used may be applied to the reactor surfaces.

Any suitable spray devices may be used which will effectively apply the solvent to the reactor surfaces as their design is not critical. For example, nozzles providing either conical or fan spray patterns may be employed, with conical spray patterns being preferred. The number of spray devices is not critical.

As shown in the FIGURE, the solvent may be supplied to reactor 10 from condenser 20 via heater 14 through spray nozzles 16. Alternately, the solvent may be fed to spray nozzles 16 from an external source.

The novel process of the present invention permits the production of concentrated cyanuric slurries in the reactor without the undesired buildup of heavy deposits on reactor surfaces. Thus slurries containing from 40 to about 70 percent, preferably from about 50 to about 65 percent by weight of cyanuric acid can be produced in the reactor. Production of these concentrated slurries reduces the required size of reactors, reduces the volume of solvent that has to be employed, and reduces the cost of solvent recovery. In addition, the novel process of the present invention reduces the frequency of cleaning reactors and reduces the downtime per cleaning.

Any solvent may be used in the pyrolysis process including, for example, alkyl cyclohexanols, methoxy ethoxy isopropanols, tetrahydrofurfuryl alcohol, alkyl sulfones, dialkyl sulfones, dialkyl ethers of polyalkylene glycols, alkyl pyrrolidones, cycloalkyl pyrrolidones, diphenyl oxide, and alkyl oxazolidinones.

Processes for the pyrolysis of urea in these solvents are described, for example, in U.S. Pat. No. 3,008,961, issued Nov. 14, 1961 to B. H. Wojcik; U.S. Pat. No. 3,065,233, issued Nov. 20, 1962, to T. R. Hopkins et al; U.S. Pat. No. 3,117,968, issued Jan. 14, 1964, to K. Merkel et al; U.S. Pat. No. 3,164,591, issued Jan. 5, 1965, to W. E. Walles et al; U.S. Pat. No. 3,563,987, issued Feb. 16, 1971, to S. Berkowitz; U.S. Pat. No. 3,635,968, issued Jan. 18, 1962, to H. Goelz et al; U.S. Pat. No. 3,810,891, issued May 14, 1974, to J. M. Lee as well as Canadian Pat. No. 687,279, issued May 26, 1964, to B. H. Wojcik; Canadian Pat. No. 729,190, issued Mar. 1, 1966, to R. M. Thomas; and Canadian Pat. No. 740,444, issued Aug. 9, 1966, to R. E. Bailey et al.

The novel process of the present invention is further illustrated by the following examples.

EXAMPLE 1

A jacketed reaction vessel was equipped with an agitator and two 60° solid cone spray nozzles in the dome of the reactor. In each of a series of nine batches, N-cyclohexyl pyrrolidone solvent was charged to the reactor. About 24 percent of the solvent charge was passed through a heater where its temperature was raised to about 200° C. and sprayed through the nozzles at a pressure of about 40 pounds per square inch onto the dome and upper walls of the reactor. After heating all the solvent charged directly to the reactor to a temperature of 225° C., molten urea was fed to the reactor and pyrolyzed in the hot solvent to produce a suspension of cyanuric acid particles. During the reaction period, additional hot solvent was sprayed through the nozzles for a few seconds every 10 minutes. Ammonia gas was evolved during the reaction and formed a gaseous mixture with solvent vapors. The gaseous mixture was removed from the reactor, passed through a scrubber and into a condenser in which the solvent was condensed and returned to the reactor. When the concentration of cyanuric acid in the suspension had reached 40 percent by weight, the reaction was discontinued. After completing the series of nine batches, the reactor surfaces were inspected and found to be virtually free of deposits. During the reaction series, it was observed that the reaction temperature remained constant, indicating no reduction in heat transfer efficiency.

EXAMPLE 2

The procedure of Example 1 was repeated in producing eleven batches of concentrated slurries of cyanuric acid with the sole exception that hot solvent was only sprayed through the nozzles during the reaction period. Hot solvent was sprayed over the reactor surfaces for a few seconds about every 10 minutes during the reaction to provide about 20 percent of the total solvent employed. Inspection of the reactor surfaces which had been sprayed with hot solvent during the eleven batches showed almost no deposits present on these surfaces.

What is claimed is:

1. In a process for producing cyanuric acid by pyrolyzing urea in a solvent in a closed reactor having interior surfaces exposed to a gas zone, the improvement which comprises contacting said interior surfaces in said gas zone with said solvent in the presence of heat to inhibit the formation of solid deposits on said interior surfaces.

2. A process for the production of cyanuric acid by the pyrolysis of urea in a solvent in a closed reactor which comprises;
   (a) pyrolyzing said urea in a hot solvent to produce a reaction mixture comprised of solid particles of cyanuric acid, said solvent and an off-gas,
   (b) agitating said reaction mixture to form a slurry of cyanuric acid particles in said solvent and releasing said off-gas to a gas zone, during said release said off-gas entraining solid particles of cyanuric acid,
   (c) removing said off-gas from said gas zone, said off-gas contacting the interior surfaces of said gas zone during removal, and
   (d) applying said solvent in the presence of heat to said interior surfaces of said gas zone to inhibit the formation of solid deposits of said cyanuric acid on said interior surfaces.

3. The process of claim 2 in which said off-gas is comprised of ammonia and solvent vapors.

4. The process of claim 3 in which said solvent is applied by spraying means.

5. The process of claim 4 in which after step c, said off-gas is fed to a condensing means to condense said solvent vapors to form condensed liquid solvent, and employing said condensed liquid solvent in step d.

6. The process of claim 5 in which said heat is provided by heating means applied to said upper reactor surfaces.

7. The process of claim 4 in which said slurry of cyanuric acid contains from about 40 to about 70 percent by weight of cyanuric acid.

8. The process of claim 7 in which said heat is provided by hot solvent having a temperature of from about 100° to about 300° C.

* * * * *